(12) United States Patent
Ashmead et al.

(10) Patent No.: US 7,910,137 B2
(45) Date of Patent: Mar. 22, 2011

(54) METAL CARNITINE CHELATES

(75) Inventors: H. DeWayne Ashmead, Fruit Heights, UT (US); R. Charles Thompson, Peterson, UT (US)

(73) Assignee: Albion International, Inc., Clearfield, UT (US)

( * ) Notice: Subject to any disclaimer, the term of this patent is extended or adjusted under 35 U.S.C. 154(b) by 750 days.

(21) Appl. No.: 11/483,410

(22) Filed: Jul. 7, 2006

(65) Prior Publication Data

US 2006/0276538 A1 Dec. 7, 2006

Related U.S. Application Data

(63) Continuation-in-part of application No. 11/173,956, filed on Jul. 1, 2005, now abandoned, which is a continuation-in-part of application No. 10/306,711, filed on Nov. 26, 2002, now abandoned.

(60) Provisional application No. 60/334,051, filed on Nov. 28, 2001.

(51) Int. Cl.
*A61K 33/24* (2006.01)
*A61K 33/34* (2006.01)
*A61K 33/32* (2006.01)
*A61K 33/26* (2006.01)
*A61K 9/48* (2006.01)
*A61K 9/20* (2006.01)
*A61K 31/28* (2006.01)
*A61K 31/30* (2006.01)
*A61K 31/295* (2006.01)
*A61K 31/315* (2006.01)
*A01N 59/16* (2006.01)

(52) U.S. Cl. ........ 424/617; 424/630; 424/639; 424/641; 424/646; 424/655; 424/451; 514/492; 514/495; 514/499; 514/502; 514/505

(58) Field of Classification Search ............ 424/600, 424/617, 630, 639, 641, 646, 655, 675; 514/492, 514/499, 502, 505
See application file for complete search history.

(56) References Cited

U.S. PATENT DOCUMENTS

| | | | |
|---|---|---|---|
| 2,877,253 A | 3/1959 | Rummel | |
| 2,957,806 A | 10/1960 | Rummel | |
| 2,960,406 A | 11/1960 | Cardon | |
| 3,396,104 A | 8/1968 | Miller | |
| 3,463,858 A | 8/1969 | Anderson | |
| 3,775,132 A | 11/1973 | Richards, Jr. | |
| 4,020,158 A | 4/1977 | Ashmead | |
| 4,067,994 A | 1/1978 | Anderson et al. | |
| 4,103,003 A | 7/1978 | Ashmead | |
| 4,167,564 A | 9/1979 | Jensen | |
| 4,169,717 A | 10/1979 | Ashmead | |
| 4,172,072 A | 10/1979 | Ashmead | |
| 4,183,947 A | 1/1980 | Cockerill | |
| 4,216,143 A | 8/1980 | Ashmead | |
| 4,216,144 A | 8/1980 | Ashmead | |
| 4,599,152 A * | 7/1986 | Ashmead | 205/435 |
| 4,725,427 A | 2/1988 | Ashmead et al. | |
| 4,774,089 A | 9/1988 | Ashmead | |
| 4,830,716 A * | 5/1989 | Ashmead | 205/457 |
| 4,863,898 A * | 9/1989 | Ashmead et al. | 514/6 |
| 5,162,369 A | 11/1992 | Ashmead et al. | |
| 5,270,297 A | 12/1993 | Paul et al. | |
| 5,292,538 A | 3/1994 | Paul et al. | |
| 5,292,729 A | 3/1994 | Ashmead | |
| 5,516,925 A | 5/1996 | Pedersen et al. | |
| 5,596,016 A | 1/1997 | Ashmead et al. | |
| 5,614,553 A | 3/1997 | Ashmead et al. | |
| 5,882,685 A | 3/1999 | Ashmead | |
| 5,888,553 A | 3/1999 | Grant et al. | |
| 5,976,579 A | 11/1999 | McLean | |
| 6,114,379 A | 9/2000 | Wheelwright et al. | |
| 6,159,530 A | 12/2000 | Christiansen et al. | |
| 6,166,071 A | 12/2000 | Ashmead et al. | |
| 6,207,204 B1 | 3/2001 | Christiansen et al. | |
| 6,280,751 B1 | 8/2001 | Fletcher et al. | |
| 6,294,207 B1 | 9/2001 | Christiansen et al. | |
| 6,299,896 B1 | 10/2001 | Cooper et al. | |
| 6,299,914 B1 | 10/2001 | Christiansen et al. | |
| 6,359,157 B2 | 3/2002 | Peter et al. | |
| 6,426,424 B1 | 7/2002 | Ashmead et al. | |
| 6,458,981 B1 | 10/2002 | Ashmead et al. | |
| 6,518,240 B1 * | 2/2003 | Pedersen et al. | 514/2 |
| 6,614,553 B2 | 9/2003 | Nakami et al. | |
| 6,710,079 B1 * | 3/2004 | Ashmead et al. | 514/492 |
| 6,716,814 B2 * | 4/2004 | Ericson et al. | 514/6 |
| 2005/0239763 A1 * | 10/2005 | Motyka et al. | 514/184 |
| 2006/0013892 A1 * | 1/2006 | Ashmead | 424/600 |
| 2006/0289775 A1 * | 12/2006 | Inbar | 250/370.11 |

FOREIGN PATENT DOCUMENTS

CN 1052412 6/1997

OTHER PUBLICATIONS

Aurich et al Preparation of 3-dehydrocarnitine, Hoppe-Seyler's Zeitschrift fuer Physiologische Chemie, 1968, vol. 349 No. 10, pp. 1310-1312 (ABS).*
United States/Japan Seminar on Thiamin 1974, New York; Wiley, c1976, pp. 12, 16, 20, 23, 46.
Abstract: Zimatkino TI, Chemikevich IP, Zimalkin SM and Deitrich RA, Thiamin Status in Liver and Brain of Rats Genetically Selected for Different Sensitivity to Hypnotic Effect of Alcohol, Alcoholism: Clinical and Experimental Research (Alcohol Clin Exp Res) Nov. 2000 vol. 24(10), pp. 1620-1624.

(Continued)

*Primary Examiner* — Alton N Pryor
(74) *Attorney, Agent, or Firm* — Thorpe North & Western LLP

(57) ABSTRACT

Metal carnitine chelates comprising carnitine chelated to a nutritionally relevant metal can be used for general nutrition as well as well as to treat a variety of health related problems and symptoms. For example, metal carnitine chelates can be used to maintain good cardiovascular health, increase male fertility, enhance weight loss, provide mineral and/or carnitine supplements for mineral- and/or carnitine-deficient subjects, and reduce alcohol dependency and associated symptoms. Nutritionally relevant metals that can be used include copper, zinc, magnesium, calcium, iron, chromium, and manganese, to name a few.

45 Claims, No Drawings

OTHER PUBLICATIONS

Synthesis and Characterization of Novel Vitamin B1 Metal Complexes, Inorganic Chemica Acta, (1981) vol. 55, pp. 177-178.

Metal Chelates of Thiamineorthophosphoric Acid-Ester Chloride Hydrochloride and Thiamine PyrophosphatJoue, Journal of Inorganic and Nuclear Chemistry, Sep. 1977, vol. 40, pp. 2110-2113.

Zimatkino TI, Chernikevich IP, Zimatkin SM and Deitrich RA, "Thiamine Status in Liver and Brain of Rats Genetically Selected for Different Sensitivity to Hypnotic Effect of Alcohol," Alcohol Clin Exp Res, Nov. 2000, pp. 1620-1624, vol. 24(10).

Adamson, Chris, "Wernicke's Encephalopathy," Indiana State University Website (http://web.indstate.edu/thcme/anderson/CAD.html), 2001, 5 pages.

The Encyclopedia of Chemistry, 2nd ed. Van Nostrand Reinhold co., NY, 1966, pp. 206-207. 271-273.

Thiamin History, Georgia State University Website (http://chemistry.gsu.edu/galctone/vitamins.bl).

Gubler, et al., Thiamine, 1974, New York; Wiley, c1976, pp. 12, 16, 20, 23, 46.

Aurich et al., "Preparation of 3-dehydrocarnitine," 1968, Hoppe-Seyler's Zeitschrift fuer Physiologishe Chemie, vol. 349 No. 10, pp. 1310-1312. (Full reference unavailable, cited in priority application by examiner.).

Bencini, Alessandro and Elena Borghi, "Complexes of Vitamin B1 with Transition Metal Ions. Crystal and Molecular Structure of Zn(Thiamine)Cl3 O • O.4H2O," Inorganica Chimica Acta (1987) pp. 85-91. vol. 135.

Cramer, Roger E., Ruby S. Evangelistaand Richard B. Maynard, "Metal Ion Complexes of Thiamin," Annals of the New YorkAcadamy of Sciences, Jan. 1982, p. 466, vol. 378.

Fridman et al., "Mixed-ligand Compounds of Copper with Glycine and Biologically Active Phosphates," Soviet Journal of Coordination Chemistry = Koordinatsionnaia Khimiia, 1985, 150-155, 11(2).

Hadjiliadis, Nick, et al., "Complexes of Tetrahydrothiamine and its Phosphate Esters with Chromium(III), Iron(III), Cobalt(II), Nickel(II) and Copper(II)," Bull. Soc. Chim. Belg.,1989, pp. 223-235, vol. 98.

Hoyumpa, Anastacio M., Jr., "Characterization of Normal Intestinal Thiamin Transport in Animals and Man," Annals of the New YorkAcademy of Sciences, Jan. 1982, pp. 337-341, vol. 378.

Hu, Ning-Hai, "A novel metal-thiamine complex with a cyclic dimer formed by metal-bridged two thiamine ligands. Crystal structure of [Mn(thiamine)Cl2(H2O)]2[thiamine]2Cl4 • 2H2O," Inorganica Chimica Acta, 1991, pp. 209-214, vol. 185.

Jain et al., "Voltammetric study of zinc complexes with L-amino acids and vitamin," 1999, J. of the Institution of Chemists, vol. 71, No. 1, pp. 5-9.

Katz, Hyman B. and Kenneth Kustin, "Thiamine Pyrophosphate-Metal Ion Complexation: Equilibrium and Kinetics," Biochemica et Biophysica Acta, 1973, pp. 235-248, vol. 313.

Khan et al. "Polarographic studies of mixed ligand complexes of Zinc (II) with L-amino acids and vitamin B1," 1993, J. of Indian Council of Chemists, vol. 9, No. 2, pp. 21-31.

Leevy, Carroll M., "Thiamin Deficiency and Alcoholism, Thiamine: Twenty Years of Progress," Annals of the New YorkAcademy of Sciences, Jan. 1982, pp. 316-325, vol. 378.

Liubimov BI et al., "Chronic alcoholic intoxications in animals or a model for studying the safety of new anti-alcoholic agents (abstract)," Farmakol toksiol 46:98-102, Physiological Abstract 9010 (1983).

Louloudi, M. et al.,"Structural aspects of thiamine, its derivatives and their metal complexes in relation to the enzymatic action of thiamine enzymes," Coordination Chemistry Reviews,1994, pp. 429-468, vol. 135/136.

Malandrinos, G. et al., "Zinc(II) and cadmium(II) metal complexes of thiamine pyrophosphate and 2-($\alpha$-hydroxyethyl)thiamine pyrophosphate: models for activation of pyruvate decarboxylase," Journal of Biological Inorganic Chemistry (JBIC), Jan. 2000, pp. 218-226, vol. 5.

Author Unknown, "Metal Chelates of Thiamineorthophosphoric Acid-Ester Chloride Hydrochloride and Thiamine Pyrophosphate," Journal of Inorganic and Nuclear Chemistry, Sep. 1977, pp. 2110-2113,vol. 40.

Venkatesha, T.V.et al., "Industrial Zinc Sulphate Plating Baths—Basic Studies, B. Electrochem," Oct. 1989, pp. 733-736, vol. 5(10).

Pires, Rita G.W et al., "The Contribution of Mild Thiamine Deficiency and Ethanol Consumption to Central Cholinergic Parameter Dysfunction and Rats' Open-Field Performance Impairment," Pharmacology, Biochemistry and Behavior, 2001, pp. 227-235, vol. 70.

Spector, Reynold, "Thiamin Homeostasis in the Central Nervous System," Annals of the New YorkAcademy of Sciences, Jan. 1982, pp. 344-353, vol. 378.

Adeyemo, Adegboye Olubowale, "Synthesis and Characterization of Novel Vitamin B1 Metal Complexes," Inorganica Chemica Acta, 1981, pp. 177-178, vol. 55.

\* cited by examiner

METAL CARNITINE CHELATES

The present application is a Continuation-In-Part of U.S. patent application Ser. No. 11/173,956, filed on Jul. 1, 2005, which is a Continuation-In-Part of U.S. patent application Ser. No. 10/306,711, filed on Nov. 26, 2002, which claims the benefit of U.S. Provisional Application No. 60/334,051 filed on Nov. 28, 2001, each of which is incorporated herein by reference in its entireties.

FIELD OF THE INVENTION

The present invention is drawn to compositions and methods for improving and maintaining health. More specifically, the present invention is drawn to carnitine chelates and their use in nutrition and in treating a variety of health conditions.

BACKGROUND OF THE INVENTION

Chelates are generally produced by the reaction between ligands and metal ions having a valence of two or more to form a ring structure. In such a reaction, the electrons available from the electron-donating group of the ligand can generally neutralize the positive electrical charge of the metal ion.

Specifically, the term "chelate" has been defined as a combination of a metallic ion bonded to one or more ligands to form a heterocyclic ring structure. Under this definition, chelate formation through neutralization of the positive charge(s) of the metal ion may be through the formation of ionic, covalent, or coordinate covalent bonding. An alternative and more modern definition of the term "chelate" requires that the metal ion be bonded to the ligand solely by coordinate covalent bonds forming a heterocyclic ring. In either case, both are definitions that describe a metal ion and a ligand forming a heterocyclic ring. Chelation can be confirmed and differentiated from mixtures of components by infrared spectra through comparison of the stretching of bonds or shifting of absorption caused by bond formation.

As applied in the field of mineral nutrition, there are certain "chelated" products that are commercially utilized. The first is referred to as a "metal proteinate." The American Association of Feed Control officials (AAFCO) has defined a "metal proteinate" as the product resulting from the chelation of a soluble salt with amino acids and/or partially hydrolyzed protein. Such products are referred to as the specific metal proteinate, e.g., copper proteinate, zinc proteinate, etc. Sometimes, metal proteinates are even referred to as amino acid chelates, though this characterization is not completely accurate.

The second product, referred to as an "amino acid chelate," when properly formed, is a stable product having one or more five-membered rings formed by a reaction between the amino acid and the metal. The American Association of Feed Control Officials (AAFCO) has also issued a definition for amino acid chelates. It is officially defined as the product resulting from the reaction of a metal ion from a soluble metal salt with amino acids having a mole ratio of one mole of metal to one to three (preferably two) moles of amino acids to form coordinate covalent bonds. The average weight of the hydrolyzed amino acids must be approximately 150 and the resulting molecular weight of the chelate must not exceed 800. The products are identified by the specific metal forming the chelate, e.g., iron amino acid chelate, copper amino acid chelate, etc.

In further detail with respect to amino acid chelates, the carboxyl oxygen and the α-amino group of the amino acid each bond with the metal ion. Such a five-membered ring is defined by the metal atom, the carboxyl oxygen, the carbonyl carbon, the α-carbon and the α-amino nitrogen. The actual structure will depend upon the ligand to metal mole ratio and whether the carboxyl oxygen forms a coordinate covalent bond or an ionic bond with the metal ion. Generally, the ligand to metal molar ratio is at least 1:1 and is preferably 2:1 or 3:1. However, in certain instances, the ratio may be 4:1. Most typically, an amino acid chelate with a divalent metal can be represented at a ligand to metal molar ratio of 2:1 according to Formula 1 as follows:

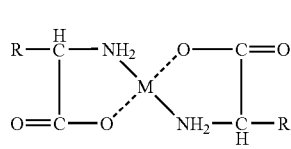

Formula 1

In the above formula, the dashed lines represent coordinate covalent bonds, covalent bonds, or ionic bonds. Further, when R is H, the amino acid is glycine, which is the simplest of the α-amino acids. However, R could be representative of any other side chain that, when taken in combination with the rest of the ligand structure(s), results in any of the other twenty or so naturally occurring amino acids derived from proteins. All of the amino acids have the same configuration for the positioning of the carboxyl oxygen and the α-amino nitrogen with respect to the metal ion. In other words, the chelate ring is defined by the same atoms in each instance, even though the R side chain group may vary.

With respect to both amino acid chelates and metal proteinates, the reason a metal atom can accept bonds over and above the oxidation state of the metal is due to the nature of chelation. For example, at the α-amino group of an amino acid, the nitrogen contributes both of the electrons used in the bonding. These electrons fill available spaces in the d-orbitals forming a coordinate covalent bond. Thus, a metal ion with a normal valency of +2 can be bonded by four bonds when fully chelated. In this state, the chelate is completely satisfied by the bonding electrons and the charge on the metal atom (as well as on the overall molecule) is zero. As stated previously, it is possible that the metal ion can be bonded to the carboxyl oxygen by either coordinate covalent bonds or ionic bonds. However, the metal ion is preferably bonded to the α-amino group by coordinate covalent bonds only.

The structure, chemistry, bioavailability, and various applications of amino acid chelates are well documented in the literature, e.g. Ashmead et al., Chelated Mineral Nutrition, (1982), Chas. C. Thomas Publishers, Springfield, Ill.; Ashmead et al., Intestinal Absorption of Metal Ions, (1985), Chas. C. Thomas Publishers, Springfield, Ill.; Ashmead et al., Foliar Feeding of Plants with Amino Acid Chelates, (1986), Noyes Publications, Park Ridge, N.J.; U.S. Pat. Nos. 4,020,158; 4,167,564; 4,216,143; 4,216,144; 4,599,152; 4,725,427; 4,774,089; 4,830,716; 4,863,898; 5,292,538; 5,292,729; 5,516,925; 5,596,016; 5,882,685; 6,159,530; 6,166,071; 6,207,204; 6,294,207; 6,614,553; each of which are incorporated herein by reference.

One advantage of amino acid chelates in the field of mineral nutrition is attributed to the fact that these chelates are readily absorbed from the gut and into mucosal cells by means of active transport. In other words, the minerals can be absorbed along with the amino acids as a single unit utilizing the amino acids as carrier molecules. Therefore, the problems associated with the competition of ions for active sites and the suppression of specific nutritive mineral elements by others can be avoided.

However, traditional amino acid chelates provide only one class of ligands that can be used to benefit human and other animal nutrition. As such, it would be beneficial to utilize ligands that include amino groups and acid groups other than the twenty naturally occurring amino acids in forming chelates, thereby expanding the possible ligands that can be used in the fields of general nutrition field and treatment.

SUMMARY OF THE INVENTION

It has been recognized that the metal carnitine chelates can be administered to subjects for various nutritional and therapeutic purposes. In accordance with this, a metal carnitine chelate can comprise carnitine chelated to a nutritionally relevant metal at a 1:1 to 4:1 molar ligand to metal ratio. In another embodiment, the metal carnitine chelate can be present as part of composition for delivering a mineral and carnitine to a subject. The composition can include the metal carnitine chelate and a carrier, along with other optional ingredients. Further, a method of providing a therapeutic effect in a subject can comprise administering a metal carnitine chelate to a subject.

DETAILED DESCRIPTION OF THE PREFERRED EMBODIMENT(S)

Before the present invention is disclosed and described, it is to be understood that this invention is not limited to the particular process steps and materials disclosed herein because such process steps and materials may vary somewhat. It is also to be understood that the terminology used herein is used for the purpose of describing particular embodiments only. The terms are not intended to be limiting because the scope of the present invention is intended to be limited only by the appended claims and equivalents thereof.

It is to be noted that, as used in this specification and the appended claims, the singular forms "a," "an," and "the" include plural referents unless the context clearly dictates otherwise.

The term "naturally occurring amino acid" or "traditional amino acid" shall mean amino acids that are known to be used for forming the basic constituents of proteins, including alanine, arginine, asparagine, aspartic acid, cysteine, cystine, glutamine, glutamic acid, glycine, histidine, hydroxyproline, isoleucine, leucine, lysine, methionine, ornithine, phenylalanine, proline, serine, threonine, tryptophan, tyrosine, valine, and combinations thereof.

The term "amino acid chelate" is intended to cover traditional amino acid ligands, i.e., those used in forming proteins. The amino acid chelate is meant to include metal ions bonded to proteinaceous ligands forming heterocyclic rings. Between the carboxyl oxygen and the metal, the bond can be covalent or ionic, but is preferably coordinate covalent. Additionally, at the α-amino group, the bond is typically a coordinate covalent bond. Proteinates of naturally occurring amino acids are included in this definition.

The term "proteinate" when referring to a metal proteinate is meant to include compounds where a nutritionally relevant metal is chelated or complexed to hydrolyzed or partially hydrolyzed protein forming a heterocyclic ring. Coordinate covalent bonds, covalent bonds and/or ionic bonding may be present in the chelate or chelate/complex structure. As used herein, proteinates are included when referring to amino acid chelates.

The term "nutritionally relevant metal" is meant to mean any divalent or trivalent metal that can be used as part of a nutritional supplement, is known to be beneficial to humans, and/or is substantially non-toxic when administered in traditional amounts, as is known in the art. Examples of such metals include copper, zinc, manganese, magnesium, iron, chromium, calcium, vanadium, and the like.

The term "carnitine" is meant to include the physiologically active L isomer that is commonly administered to improve or maintain a variety of health conditions, as is known in the art, and all functional carnitine derivatives including acetyl-L-carnitine.

The term "carnitine chelate" is meant to include metal ions bonded to carnitine ligands forming one or more heterocyclic rings. Complexes that do not form ring structures with the metal as a closing member are not considered to be carnitine chelates and are specifically excluded from this definition in accordance with embodiments of the present invention.

The terms "metal carnitine chelate" or "carnitine metal chelate" can be used interchangeably. Additionally, a specific metal can be substituted for the metal of the term. When discussing molar ratios, the first number of the ratio will always refer to the carnitine ligand and the second number will always refer to the metal. Thus, a 2:1 molar ratio of a metal carnitine chelate indicates two moles of carnitine to one mole of metal.

In accordance with this, a metal carnitine chelate can comprise carnitine chelated to a nutritionally relevant metal at a 1:1 to 4:1 molar ratio. In another embodiment, the metal carnitine chelate can be present as part of composition for delivering a mineral and carnitine to a subject. The composition can include the metal carnitine chelate and a carrier, along with other optional ingredients. Further, a method of providing a therapeutic effect in a subject can comprise administering a metal carnitine chelate to a subject.

Carnitine is a somewhat unique molecule in that it has a methylated tertiary nitrogen that carries a fixed positive charge at its tertiary amine group. The tertiary nitrogen is typically balanced by an equal negative charge on the carboxylate group of the molecule. In this configuration, the molecule is said to be zwitterionic because of two full opposite charges carried by the molecule. A somewhat unique characteristic of carnitine comes from the fact that it typically exists in this zwittwerionic form at most pH levels. All of the naturally occurring or traditional amino acids can form zwitterions, but the ionization of most amino acids is dependant on the pH of the solution in which they are dissolved. Except in low pH environments, carnitine typically exists as a zwitterion independent of the solution pH.

The carboxylate group of carnitine is typically ionized; the negative charge present can be shared by both of the oxygen atoms of the carboxylate group. There are two possible resonance structures for an ionized carboxylate group, where one or the other oxygen carries the negative charge. In reality the charge resonates back and forth between the oxygen atoms creating a structure where the two oxygen molecules share the negative charge. With respect to carnitine, the "fixed" zwitterionic charge on carnitine has a full positive charge on the nitrogen, and a resonance or shared full negative charge on the carboxylate group.

Small amounts of carnitine can be synthesized by the body from two different amino acids, e.g., lysine/methionine; however, the majority of carnitine used by the body comes from nutritional sources. Carnitine is found most abundantly in meat, specifically red meat. Carnitine's structure resembles that of an amino acid, in that carnitine has a tertiary amino group and a carboxylic acid group. Physiologically, carnitine's most significant role in the body is in fat metabolism. Specifically, a converted form of carnitine helps provide energy to the body by transporting fatty acids into the mitochondria of cells.

Specifically, carnitine consists of a tertiary amino, hydroxy, and carboxylic acid functional groups, as shown in Formula 1 below:

Formula 1

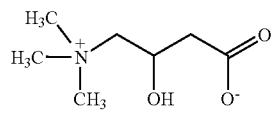

Despite the fact that the amine group of the carnitine molecule is quaternary, carnitine chelates can still be formed. In one such ring, the carboxyl oxygen and the β-hydroxy group of carnitine can each bond with the metal ion. Such a ring is defined by the metal atom, the carboxyl oxygen, the carbonyl carbon, the α-carbon, β-carbon, and the β-hydroxy oxygen, as shown by Structure A in Formulas 2 and 3 below. In an alternative embodiment, the ring structure can be formed by the metal atom and both carboxyl oxygens, as shown by Structure B in Formulas 2 and 3. The actual structure will depend upon the ligand to metal mole ratio and whether the carboxyl oxygen forms a covalent bond or an ionic bond with the metal ion. Generally, the ligand to metal molar ratio is at least 1:1 or 2:1, but can be 3:1 or even 4:1 in some more rare embodiments. In one embodiment, a carnitine chelate with a divalent metal can be represented at a ligand to metal molar ratio of 2:1 according to Formula 2 as follows:

Formula 2

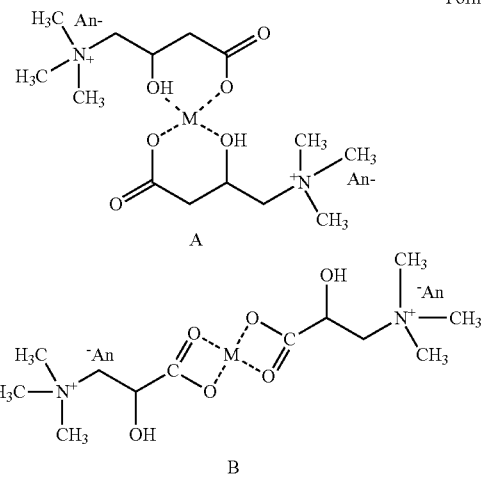

Additionally, the carnitine can be bonded to the metal atom in a 1:1 ratio, as shown in Formula 3 below:

Formula 3

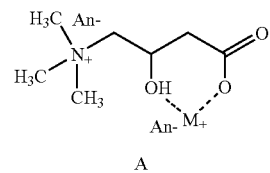

A

-continued

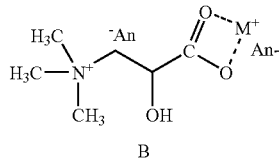

B

In the above formulas, the dashed lines represent coordinate covalent bonds, covalent bonds, or ionic bonds. However, in all cases, the metal and the ligand form a ring structure, which is an essential feature of a chelate.

In Formulas 2 and 3 above, M can be Cu, Zn, Ca, Mg, Fe(II), or Mn, for example; and An can be the salt form of chloride, nitric acid, acetic acid, succinic acid, ascorbic acid, fumeric acid, citric acid, malic acid, oxalic acid, lactic acid, benzoic acid, tartaric acid, adipic acid, phosphoric acid, propionic acid, or sulfuric acid. Other nutritionally relevant metals (M) and anions (An⁻) can be used as would be apparent to one skilled in the art after considering the present disclosure. For example, it is notable that divalent metals are exemplified in Formulas 2 and 3; however, this is not required. Trivalent metals, such as Fe(III) and Cr, and metals having higher valences, such as vanadium, can also be used to form appropriately configured chelates.

As shown in Formulas 2 and 3 above, a metal ion can be chelated to the carnitine ligand in one of two ways. In one embodiment, the metal can be bound only to the carboxylate end of two carnitine molecules in a 2:1 carnitine to metal molar ratio embodiment (Structure B of Formula 2) or to the carboxylate end of one carnitine molecule in a 1:1 carnitine to metal molar ratio embodiment (Structure B of Formula 3). This type of bonding is common for ionized carboxylate groups, and still meets a broader definition of a chelate as it provides a ring structure. Though a double bond is shown at the carboxylate group, in actuality, charge sharing occurs between the two oxygen atoms and a true double bond does not typically exist.

Alternatively, the negative charge on the carboxylate group can be fixed to one of its oxygen atoms as a result of chelation to the metal ion. The hydroxyl group on the β-carbon atom of carnitine can also participate in the chelation bonding of carnitine to the metal ion, creating a more traditional metal ligand chelate. Even though the hydroxyl group is still shown to maintain its hydrogen atom upon chelation, a ring structure can still be formed by attraction between the metal and the hydroxyl group. A 2:1 carnitine to metal molar ratio (Structure A of Formula 2) or a 1:1 carnitine to metal molar ratio (Structure A of Formula 3) can be formed.

With respect to Structures A and B of Formula 3, even after chelation, the charge on the metal (M) is still not satisfied, and therefore, can form a salt with the anion (An⁻) present in the reaction. In other words, when the carboxylate group of carnitine is bonded to a metal ion, the positive charge also is typically balanced by an equal negative charge. This can be achieved by using a metal salt that dissociates and balances the charge on both the tertiary amine of the carnitine and the metal. This is not necessary with many of the 2:1 embodiments, as the metal charges can be balanced by the second carnitine ligand, if the metal is divalent. If the metal is trivalent and the ligand to metal molar ratio is 2:1, the metal (M) can be counter-balanced by an anion (An⁻) similar to that shown in the 1:1 embodiment.

Carnitine chelates can be used in many different therapeutic or nutritional applications. For example, a carnitine chelate can be used to improve the ability of a subject to exercise. Carnitine is known to help the body in energy production by transporting fatty acids into the mitochondria of the cell. Carnitine also helps eliminate waste products in the cell by transporting them out of the mitochondria. An increased ability to metabolize fat and eliminate waste products would allow the body to exercise at a more efficient level. Exercise also depletes the body of minerals. Therefore, an individual who exercises frequently, would benefit from an additional source of carnitine as well as an extra source of minerals. In one embodiment, carnitine can be used as a chelating ligand for a nutritionally relevant metal, such as copper, zinc, magnesium, and/or manganese, and these metals can also contribute to improved exercise performance. Alternatively, it may be desired to coadminister other components that aid in improving exercise energy or results. Other sources for improving exercise energy or results include creatine, vitamins, electrolytes, and other exercise supplements as known on the art.

Carnitine chelates can also be used to help maintain good cardiovascular health. Carnitine provides energy to the heart through fat metabolism. Additionally, carnitine has been linked to maintaining cardiovascular health in general. Patients who have suffered from heart attacks have benefited from carnitine treatment by reducing the incidence of subsequent heart attacks. In conjunction with this, there are many minerals, such as copper, calcium, zinc, magnesium and/or manganese, which can be used to maintain good cardiovascular health. Therefore, an individual wishing to maintain good cardiovascular health would benefit from the use metal carnitine chelates in order to supplement both carnitine and mineral levels. Alternatively, it may be desired to co-administer other components that aid in maintaining good cardiovascular health to a subject in need thereof. Other sources that can be used for maintaining good cardiovascular health include vitamins, exercise, and proper nutrition.

Carnitine chelates can also help an individual to lose weight. As previously cited, carnitine helps the body metabolize fat by transporting fatty acids into the mitochondria of the cell to produce energy. Increasing the body's ability to metabolize fat can help an individual lose weight. Additionally, individuals desiring to lose weight often increase their level of exercise and/or decrease their food consumption. As previously cited, an individual who exercises can benefit from taking a supplement of carnitine and minerals. Likewise, a decrease in food consumption can result in a lower intake of carnitine and minerals; therefore, such an individual would further benefit from taking a supplement of carnitine and minerals. In one embodiment, suitable minerals that can be used for this purpose include calcium, zinc, magnesium, chromium, vanadium, and/or manganese. It may also be desired to co-administer other components with the metal carnitine chelate in order to further, promote weight loss. Other sources for helping an individual lose weight include vitamins, exercise, diet, and proper nutrition.

Carnitine chelates can also enhance male fertility. Carnitine has been linked to male fertility based on the finding that sperm cells have an increased concentration of carnitine, which relates to the ability of the sperm to metabolize fat into energy; providing sperm motility. As such, by increasing the sperms motility through additional sources of carnitine, fertility can be increased. Additionally, certain minerals that are commonly used to increase male fertility, such as calcium, zinc, magnesium, and/or manganese, can be chelated to carnitine for achieving this therapeutic effect. It may be also desired to co-administer other components that aid in male fertility.

Carnitine chelates can be used to supplement carnitine and mineral deficient individuals. Certain groups of people can be characterized as carnitine-deficient. For example, vegetarians do not eat meat, which is the most carnitine abundant food group. Athletes tend to eat carbohydrate rich foods before competing in events at the expense of carnitine rich foods, like meat. Elderly people tend to eat less as they age, resulting in less intake of carnitine. Infants that are deprived of the carnitine in their mother's breast milk must rely on supplemental carnitine often found in formula. Additionally, these restricted eating habits can leave these groups lacking in minerals as well. In accordance with the methods of the present invention, carnitine chelates can be used to provide a supplemental source of carnitine and minerals to help maintain a healthy diet for athletes, elderly people, infants, and/or vegetarians, for example. In one embodiment, carnitine can be used as a chelating ligand for a nutritionally relevant metal, such as calcium, zinc, magnesium, manganese, iron, chromium, copper, etc., and this composition can be effective in maintaining proper carnitine and mineral levels. This being stated, it may be desired to co-administer other components that aid in maintaining a healthy, well-balanced diet.

Carnitine chelates can also be used to reduce alcohol dependency. Copper, zinc, and manganese are preferred metals for use to reduce alcohol desire and/or alcohol dependency in humans due to the fact that ethanol abuse is believed to exacerbate deficiencies of these metals, particularly with respect to copper and zinc. In one embodiment, carnitine can be used as a chelating ligand for copper, zinc, and/or manganese, and this composition can be effective in reducing alcohol desire and/or dependency. It may also be desirable to co-administer other components that aid in the alcohol dependency reduction. For example, amino acid chelates can be admixed or blended with the metal carnitine chelate(s), wherein the amino acid chelate comprises a naturally occurring amino acid ligand and a metal selected from the group consisting of copper, zinc, and manganese, and wherein the amino acid to metal molar ratio is from 1:1 to 4:1. These admixtures can be present at from 40:1 to 1:40 by weight.

EXAMPLES

The following examples are illustrative of a present method of reducing alcohol dependency in humans, as well as compositions that can be used for the same. As such, the following examples should not be considered as limitations of the present invention, but merely demonstrate the effectiveness of the methods and compositions described herein.

Example 1

Preparation of 1:1 Carnitine Copper Chelates

A 1:1 molar ratio of a copper carnitine chelate can be prepared by reacting a 0.5 molar solution of $CuCl_2$ (67.2 g/L) and a 0.5 molar solution of carnitine (80.6 g/L) in an aqueous solution, as shown below:

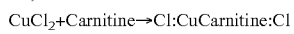

$CuCl_2$+Carnitine→Cl:CuCarnitine:Cl

In accordance with the above reaction scheme, the following procedures were followed to obtain about 147.8 g of total dissolved solids. Specifically, 0.5 moles (80.6 g) of carnitine was dissolved in one liter of water, and the mixture was brought to 55-60° C. Next, 0.5 moles (67.2 g) of cupric chloride was added to the mixture, and the mixture was allowed to react for a total of 4 hours. After the 4 hour reaction time, the composition was cooled 40° C. and spray dried to obtain about 147.8 g of a 1:1 copper carnitine chelate product, as shown in Formula 3, at 100% yield.

Example 2

Preparation of other 1:1 Metal Carnitine Chelates

The same process set forth in Example 1 above can be carried out using different metal salts or oxides as the metal source. Some metal sources and amounts used in the process are exemplarily set forth in Table 1 below:

TABLE 1

| Metal Source | Amount (g/L) |
| --- | --- |
| ZnO | 40.69 |
| $ZnCl_2$ | 68.14 |
| $ZnCO_3$ | 62.70 |
| $MgCl_2$ | 47.60 |
| MgO | 20.15 |
| CaO | 28.04 |
| $FeSO_4$ | 75.95 |
| $Cu(OH)_2$ | 48.78 |

It is noted that the metal oxides and carbonates shown in Table 1 above may benefit from the addition of an acid to assist in causing a more complete reaction between the metal oxide or carbonate and the carnitine ligand. Additionally, acid can be added to any of the embodiments exemplified herein if desirable to achieve acceptable reaction conditions. Additionally, soy flour, rice flour, or some other inert absorbent substance can be added to the product solution in order to aid in spray drying or to provide sufficient bulk for oven drying. Chelation may be confirmable through analysis of IR spectra of reaction product.

Example 3

Preparation of 2:1 Carnitine Copper Chelates

A 2:1 molar ratio of a copper carnitine chelate can be prepared by reacting a 0.5 molar solution of $Cu(Cl)_2$ (67.2 g/L) and a 1.0 molar solution of carnitine (161.2 g/L) in an aqueous solution, as shown below:

$$Cu(Cl)_2 + 2 Carnitine \rightarrow Cu(Carnitine:Cl)_2$$

In accordance with the above reaction scheme, the following procedures were followed to obtain about 228.4 g of total dissolved solids. Specifically, 1.0 moles (161.2 g) of Carnitine was dissolved in one liter of water, and the mixture was brought to 55-60° C. Next, 0.5 moles (67.2 g) of cupric chloride was added to the mixture and allowed to react for a total of 4 hours. After 4 hours of reaction time, the composition was cooled to 40° C. and spray dried to obtain about 228.4 g of a 2:1 copper carnitine chelate, as shown in Formula 2, at 100% yield.

Example 4

Preparation of other 2:1 Carnitine Metal Chelates

The same process set forth in Example 3 above can be carried out using different metal salts or oxides as the metal source. Some metal sources and amounts used in the process are exemplarily set forth in Table 2 below:

TABLE 2

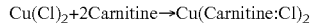

| Metal Source | Amount (g/L) |
| --- | --- |
| ZnO | 40.69 |
| $ZnCl_2$ | 68.14 |
| $ZnCO_3$ | 62.70 |
| $MgCl_2$ | 47.60 |
| MgO | 20.15 |
| CaO | 28.04 |
| $FeSO_4$ | 75.95 |

It is noted that the metal oxides and carbonates shown in Table 2 above may benefit from the addition of an acid to assist in causing a more complete reaction between the metal oxide or carbonate and the carnitine ligand. Additionally, acid can be added to any of the embodiments exemplified here if desirable to achieve acceptable reaction conditions. Additionally, soy flour, rice flour, or some other inert absorbent substance may be added to the product solution in order to aid in spray drying or to provide sufficient bulk for oven drying. Chelation can be confirmable through analysis of IR spectra of reaction product.

Example 5

Preparation of 2:1 Carnitine Chromium Chelates

To prepare a 2:1 molar ratio carnitine chromium chelate, 1.23 moles (197.66 g) of L-carnitine is dissolved in 600 mL of distilled water. At this point, 0.5 moles (133.225 g) of $CrCl_3 \cdot 6H_2O$ is added to the solution while continuously stirring. After approximately 2 hours, all of the chromium chloride goes into solution. While continually stirring, rice flour (25 g) is added to serve as an inert absorbent for more efficient spray drying. The solution is then spray-dried to yield a 2:1 carnitine chromium chelate.

Example 6

Preparation of 2:1 Carnitine Magnesium Chelates

To prepare a 2:1 molar ratio carnitine magnesium chelate, 0.98 moles (157.42 g) of L-carnitine is dissolved in 800 mL of distilled water by continuous stirring. At this point, 1.6 moles (189.82 g) of $MgSO_4$ is added and the solution is stirred until clear. The solution is allowed to stand while the magnesium and carnitine react, forming a precipitate. The product is then spray-dried to yield a 2.65:1 carnitine magnesium chelate.

It is to be understood that the above-described compositions and arrangements are only illustrative of the application of the principles of the present invention. Numerous modifications and alternative arrangements may be devised by those skilled in the art without departing from the spirit and scope of the present invention. Thus, while the present invention has been fully described above with particularity and detail in connection with what is presently deemed to be the most practical and preferred embodiments of the invention, it will be apparent to those of ordinary skill in the art that numerous modifications, including, but not limited to, variations in materials, form, function, and use may be made without departing from the principles and concepts set forth herein.

What is claimed is:

1. A metal carnitine chelate, comprising carnitine chelated to a nutritionally relevant metal at a 1:1 to 4:1 molar ratio.

2. A metal carnitine chelate as in claim 1, wherein the metal is copper.

3. A metal carnitine chelate as in claim 1, wherein the metal is zinc.

4. A metal carnitine chelate as in claim 1, wherein the metal is manganese.

5. A metal carnitine chelate as in claim 1, wherein the metal is magnesium.

6. A metal carnitine chelate as in claim 1, wherein the metal is calcium.

7. A metal carnitine chelate as in claim 1, wherein the metal is iron.

8. A metal carnitine chelate as in claim 1, wherein the metal is chromium.

9. A metal carnitine chelate as in claim 1, wherein the metal is vanadium.

10. A metal carnitine chelate as in claim 1, wherein the carnitine to metal molar ratio is about 1:1.

11. A metal carnitine chelate as in claim 1, wherein the carnitine to metal molar ratio is about 2:1.

12. A composition for delivering a mineral and carnitine to a subject, comprising:
  a metal carnitine chelate including carnitine chelated to and a nutritionally relevant metal at a 1:1 to 4:1 molar ratio; and
  a carrier.

13. A composition as in claim 12, wherein the metal is selected from the group consisting of copper, zinc, manganese, magnesium, calcium, iron, vanadium, and chromium.

14. A composition as in claim 12, wherein the carnitine to metal molar ratio is about 1:1.

15. A composition as in claim 12, wherein the carnitine to metal molar ratio is about 2:1.

16. A composition as in claim 12, further including a therapeutically effective agent other than the metal carnitine chelate.

17. A composition as in claim 16, wherein the therapeutically effective agent is selected from the group consisting of a drug, a vitamin, an enzyme, an herb, and combinations thereof.

18. A composition as in claim 16, wherein the therapeutically effective agent is selected from the group consisting of a metal salt, a metal amino acid chelate, a second metal carnitine chelate, and combinations thereof.

19. A composition as in claim 12, wherein the composition is in a liquid dosage form.

20. A composition as in claim 12, wherein the composition is in a solid dosage form.

21. A composition as in claim 20, wherein the composition is in powder form.

22. A composition as in claim 20, wherein the solid dosage form is incorporated into a tablet or capsule.

23. A composition as in claim 12, wherein the carrier includes maltodextrin, rice flour, wheat starch, potato strarch, corn starch, tapioca starch, rice starch, cacia gum, fumed silica, or combinations thereof.

24. A method of providing a nutritional or therapeutic effect in a subject, comprising administering a metal carnitine chelate to a subject, said metal carnitine chelate including carnitine chelated to a nutritionally relevant metal at a 1:1 to 4:1 molar ratio.

25. A method as in claim 24, wherein the metal is selected from the group consisting of copper, zinc, manganese, magnesium, calcium, iron, vanadium, and chromium.

26. A method as in claim 24, wherein the carnitine to metal molar ratio is about 1:1.

27. A method as in claim 24, wherein the carnitine to metal molar ratio is about 2:1.

28. A method as in claim 24, wherein the therapeutic effect includes enhancement of an ability of the subject to exercise, and the step of administering occurs prior within an hour prior to exercising.

29. A method as in claim 28, wherein the metal is selected from the group consisting of copper, zinc, magnesium, manganese, and combinations thereof.

30. A method as in claim 24, wherein the therapeutic effect includes improved cardiovascular health for the subject.

31. A method as in claim 30, wherein the metal is selected from the group consisting of calcium, magnesium, zinc, copper, and combinations thereof.

32. A method as in claim 24, wherein the therapeutic effect includes enhancing weight loss performance in the subject.

33. A method as in claim 32, wherein the metal is selected from the group consisting of calcium, zinc, magnesium, manganese, chromium, vanadium, and combinations thereof.

34. A method as in claim 24, wherein the therapeutic effect includes improving male fertility.

35. A method as in claim 34, wherein the metal is selected from the group consisting of calcium, zinc, magnesium, manganese, and combinations thereof.

36. A method as in claim 24, wherein the therapeutic effect includes enhancing carnitine levels in the blood and tissue of the subject.

37. A method as in claim 36, wherein the subject is carnitine deficient.

38. A method as in claim 24, wherein the therapeutic effect includes enhancing mineral levels in the blood and tissue of the subject.

39. A method as in claim 38, wherein the subject is deficient of a specific mineral present in the metal carnitine chelate.

40. A method as in claim 24, wherein the therapeutic effect includes reducing symptoms of alcohol desire or dependency in a human subject.

41. A method as in claim 40, wherein the metal is selected from the group consisting of copper, zinc, manganese, and combinations thereof.

42. A method as in claim 24, further comprising co-administering a therapeutically effective agent other than the metal carnitine chelate.

43. A method as in claim 42, wherein the therapeutically effective agent is a second metal carnitine chelate that includes a different metal than the metal carnitine chelate.

44. A method as in claim 42, wherein the therapeutically effective agent is selected from the group consisting of a drug, a vitamin, an enzyme, and combinations thereof.

45. A method as in claim 42, wherein the therapeutically effective agent is selected from the group consisting of a metal salt, a metal amino acid chelate, and combinations thereof.

* * * * *